(12) United States Patent
Schröder

(10) Patent No.: US 7,128,909 B2
(45) Date of Patent: Oct. 31, 2006

(54) IMMUNSTIMULATING LIPID FORMULATION

(75) Inventor: Ulf Schröder, Sundbyberg (SE)

(73) Assignee: Eurocine AB, Stockholm (SE)

( * ) Notice: Subject to any disclaimer, the term of this patent is extended or adjusted under 35 U.S.C. 154(b) by 0 days.

(21) Appl. No.: 09/147,367

(22) PCT Filed: Jun. 9, 1997

(86) PCT No.: PCT/SE97/01003

§ 371 (c)(1),
(2), (4) Date: Dec. 9, 1998

(87) PCT Pub. No.: WO97/47320

PCT Pub. Date: Dec. 18, 1997

(65) Prior Publication Data

US 2002/0012673 A1    Jan. 31, 2002

(30) Foreign Application Priority Data

Jun. 10, 1996    (SE) .................................. 9602280

(51) Int. Cl.
*A61K 39/00* (2006.01)
*A61K 39/12* (2006.01)
*A61K 39/15* (2006.01)
*A61K 39/02* (2006.01)

(52) U.S. Cl. .................. 424/184.1; 424/204.1; 424/206.1; 424/215.1; 424/236.1; 514/937

(58) Field of Classification Search ................ 424/450, 424/184.1, 400, 206.1, 209.1, 215.1, 234.1, 424/238.1; 514/937–942
See application file for complete search history.

(56) References Cited

U.S. PATENT DOCUMENTS

| 4,073,743 A | | 2/1978 | Midler et al. |
| 4,446,165 A | * | 5/1984 | Roberts ...................... 426/602 |
| 4,997,851 A | * | 3/1991 | Isaacs |
| 5,256,641 A | | 10/1993 | Yatvin et al. |
| 5,352,450 A | * | 10/1994 | Koga |
| 5,716,637 A | * | 2/1998 | Amselem |
| 5,730,989 A | * | 3/1998 | Wright |
| 5,739,118 A | * | 4/1998 | Carrano |

FOREIGN PATENT DOCUMENTS

| EP | 0 544 612 A2 | 6/1993 |
| GB | 1374325 A | 11/1974 |
| WO | WO93 06921 A1 | 4/1993 |
| WO | WO95 22989 A1 | 8/1995 |

OTHER PUBLICATIONS

Tengamnuay et al., Pharmaceutical Research. 7:127-133 (1990).

* cited by examiner

*Primary Examiner*—Gollamudi S. Kishore
(74) *Attorney, Agent, or Firm*—Bacon & Thomas PLLC

(57) ABSTRACT

A pharmaceutical formulation for parenteral or mucosal administration of antigens and/or vaccines to humans and animals, comprising monoglyceride preparations having at least 80% monoglyceride content and where the acyl group contains from 6 to 24 carbon atoms, together with fatty acids where the number of carbon atoms may be varied between 4 and 22.

7 Claims, No Drawings

IMMUNSTIMULATING LIPID FORMULATION

The present invention relates to a novel pharmaceutical formulation for administration of antigens and/or vaccines. The preferred route of administration is via the mucosal membranes, however parenteral administration may also be used. The invention also relates to the use of certain compounds (as defined below) as adjuvants or vehicles in such formulation.

BACKGROUND

An increasing number of specific antigens from different types of organisms (e.g. tumor cells, bacteria, virus and parasites) has been produced using cloning techniques over the last years. However, these antigens are frequently weak immunogens despite their high specificity.

To obtain good protection after vaccination, immune stimulating systems are needed that can enhance and activate the immune system against these weak antigens. Such immune stimulating systems are called adjuvants.

Adjuvants, presently mainly used in animal experiments, includes a highly heterogeneous group of substances; inorganic substances, oil emulsions, charged polymers, neutral substances or substances from bacteria.

There are presently large efforts in research and development in order to obtain a safe adjuvant with high efficacy to be used in humans. However, today there is presently no general adjuvant for this purpose.

Alum hydroxides and alum phosphates were the first two inorganic substances that were used in humans. The immune response obtained is a result of slow desorption of the precipitated antigen on the surface of the particle. Later it was shown that phagocyting cells were attracted by these alum salts leading to further enhancement of the immune response. However, these salts are not safe since granuloma formation has been reported (Slater et al, Br. J. Dermatol. (1982) Vol. 107, page. 103–108.). Furthermore, the alum salts can not be used for all antigens since all antigens are not adsorb on the surface.

In 1944 Freund introduced his adjuvant consisting of a mixture of vegetable oil, mineral oil, detergents and killed bacteria. The enhancement obtained was partly due to slow release of the antigen from the oil emulsion. Freunds adjuvant can however not be used in humans due to granuloma formation, induction of auto-immune reactions and the non-biodegradable mineral oil. Furthermore, the effect is difficult to control. The active substance in Freunds adjuvant has been isolated and its structure determined and shown to be N-acetyl muramyl-L-alaninisoglutamate, often called muramyl-dipeptide (MDP).

The adjuvant effect dependent of the particle size of polymetacrylate and polystyrene particles was examined on mice (Kreuter et al, Vaccine, (1986) vol 4, 125–129) by the use of ovalbumin (adsorbed on the particles) as a model antigen with subsequent assay of the immune response. The size of the particles was varied between 62 and 306 nm. The result was that smaller particles enhanced the immune response better than larger. The smaller particles gave a better effect than 0.2% $Al(OH)_3$. All preparations elicited a higher response as compared to fluid preparations. Similar experiments where particulate systems with smaller size results in a higher immune response as compared to larger particles are known in the scientific literature.

Almost all systems used today for enhancement of the immune response against antigens are particles or is forming particles together with the antigen. In the book "Vaccine Design—the subunit and adjuvant approach" (Ed: Powell & Newman, Plenum Press, 1995) all known adjuvants are described both regarding their immunological activity as well as regarding their chemical characteristics. As described in the book more than 80% of the adjuvants tested today are particles or polymers that together with the antigens (in most cases proteins) are forming particles. The type of adjuvants that not are forming particles are a group of substances that are acting as immunological signal substances and which under normal conditions consists of the substances that are formed by the immune system as a consequence of the immunological activation after administration of particulate adjuvant systems.

Using particulate systems as adjuvants, the antigens are associated or mixed with or to a matrix which has the characteristics of being slowly biodegradable. Of great importance using such matrix systems are that the matrix does not form toxic metabolites. Choosing from this point of view, the main kind of matrices that can be used are mainly substances originating from a body. With this background there are only a few systems available that fulfils these demands: lactic acid polymers, poly-amino acids (proteins), carbohydrates, lipids and biocompatible polymers with low toxicity. Combinations of these groups of substances originating from a body or combinations of substances originating from a body and biocompatible polymers can also be used. Lipids are the preferred substances since they display structures that make them biodegradable as well as the fact that they are the most important part in all biological membranes.

Lipids are characterized as polar or non-polar. The lipids that are of most importance in the present invention are the polar lipids since they have the capacity to form particulate systems in water. Another way of defining these lipids are as amphifilic due to their chemical structure with one hydrophobic and one hydrophilic part in the molecule thereby being useable as surface active substances. Examples of main groups of polar lipids are mono-glycerides, fatty acids, phospholipids and glycosphingolipids. These main groups can be further characterized depending on the length of the acyl chain and the degree of saturation of the acyl chain. Since the number of carbon atoms in the acyl chain can be in the range of 6 to 24 and the number of unsaturated bonds can be varied there are an almost infinite number of combinations regarding the chemical composition of the lipid.

Particulate lipid systems can be further divided into the different groups as discussed in the scientific literature such as liposomes, emulsions, cubosomes, cochleates, micelles and the like.

In a number of systems the lipids may spontaneously form, or can be forced to form, stabile systems. However, under certain circumstances other surface active substances has to be introduced in order to achieve stability. Such surface active systems can be of non- lipid character but possess the characteristics of the polar lipids having hydrophobic and hydrophilic parts in their molecular structure.

Another factor that has been shown to be of importance is that lipids exhibit different physical chemical phases, these phases has in different test systems been shown to enhance uptake of biological substances after administration to mucosal membranes.

In the classical immunology and in combination with vaccination against different types of infectious agents e.g. bacteria, virus or parasites the prevailing dogma has been to administrate the vaccine subcutaneously or intramuscularly. However, research has during the last years shown that the body has a very effective immunological system that resides in the mucosa. It has been shown that you can administrate vaccines orally, nasally, rectally and vaginally. In the same way as for the classical immunization it has been shown that by mucosal vaccination there is also a need for enhancement of the immunological response by the addition of adjuvants.

In the same way as within the classical immunology where vaccines (antigens) are administered parenterally, there is within mucosal immunization a great interest in directing the immunological response towards development of humoral and/or cellular response. If you obtain a humoral response it would be important to direct the response in a way that a certain class of antibodies would be obtained. In order to obtain such a goal, specific immune stimulating agents can be added to the formulation of antigens and adjuvants.

Different types of immune stimulating substances are available. One type is represented by proteins e.g. PHA, Con A, SEA or different types of interferons or interleukines. Another type of substance is represented by MDP, as mentioned above. Additional groups can be characterized as lipid derivatives since they show molecular structures which are amphiphilic. One example of such a substance is called MPL. Another similar substance is Quil A. A number of substances that can be classified within these categories are described in the book "Vaccine Design—the subunit and adjuvant approach" as discussed above.

It would be extremely valuable to be able to make the immunization procedures more effective directing the immunological response towards a certain class or subclass of antibodies and/or to be able to induce a strong T-cell response against the antigens.

DESCRIPTION OF THE INVENTION

It has now surprisingly been found that parenteral or mucosal administration of a pharmaceutical formulation containing one or two of the following adjuvants with admixed antigens and/or vaccines improves the immune response against the admixed antigens/vaccines. Said pharmaceutical formulation for parenteral or mucosal administration of antigens and/or vaccines to an animal comprise one or more substances selected from a) monoglycerides of the general formula

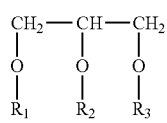

wherein $R_1$ and $R_2$ is H and $R_3$ is one acyl group containing from 6 to 24 carbon atoms, preferably 8 to 20 carbon atoms, even more preferably 14–20 carbon atoms and where the acyl chain may contain unsaturated bonds. In a monoglyceride the acyl chain is normally in the $R_1$ or $R_3$ position. However there is normally a acyl migration between the 1 and 2 carbons in the glycerol molecule resulting in approximately 90% is in the $R_3$ position and 10% in the $R_2$ position. Thus, in the present invention distilled 1-monoglycerides from Danisco Ingredients (Denmark) with a purity of more than 80% preferably more than 90%, more preferably over 95% is used. The diglyceride content is maximum 3% and triglycerides and fatty acid content is less than 1.0%. The monoglycerides according to the invention normally contains more than more than 80% of a specific fatty acid, preferably over 90%.

and
b) fatty acids of the general formula

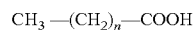

where "n" may be varied between 4 and 22, preferably 8 to 18 and where the acyl chain may contain one or more unsaturated bonds.

The formulation according to the invention may comprise additional pharmaceutical excipients selected from the one or several of the following groups; preservatives and osmotic pressure controlling agents, pH-controlling agents, organic solvents, hydrophobic agents, enzyme inhibitors, water absorbing polymers, surfactants and absorption promoters, anti-oxidative agents, and the like.

The formulation according to the invention may comprise any antigen and/or vaccine selected among all the antigen and/or vaccines relevant to humans or animals, including marine animals.

This invention discuss lipids which, when mixed with antigens, enhance the immune activity against the antigens thereby functioning as an adjuvant in various vaccine formulations. Especially the invention comprise the use of a formulation for vaccination of the mucosa which can be immunologically activated by nasal, oral, vaginal or rectal administration. The invention also comprise the use of the lipid system for parenteral administration. The use of an adjuvant such as described in the present invention, which can be used both for parenteral as well as for mucosal administration is not limited to humans. Equally important is the use within the veterinary field for the immunization of e.g. cattle, pigs, chickens and the like. Furthermore, there is a large and growing interest in applying both parenteral as well as mucosal vaccines in the field of fish farming. In this area the administration can be performed by incorporation of the formulation in the food. Furthermore, the fish may be allowed to swim for a limited period of time in the vaccine formulation containing the antigens and the adjuvants thus being immunized by the mucosal route via the gills.

In the scientific literature there are reports showing how to enhance the uptake of a biologically active substance after administration to the mucosa together with certain lipids.

As an example Li & Mitra (Pharm. Res. vol 13:1, 1996) describes the administration of insulin mixed with phospholipids in the form of liposomes to the lung. They show that the effect is dependent on the length of the acyl chain and the charge of the particle. Optimal length was 10 carbon atoms and the charge preferably positive. Even negatively charged particles were effective but neutral system were inferior.

In the same way de Haan et al (Vaccine, 13:2, 155–62, 1995) describes a mixture of liposomes and the antigen hemeagglutinin. The mixture was administered nasally to rats whereafter a positive immunological response could be detected. Gupta et al (Vaccine, 14:3, 219–25, 1995) describes that a mixture of diphtheria toxoid together with a non-phospholipid based liposom system administrated parenterally to rabbits results in an immune response which was at the same level as the marketed product which was Alum-adsorbed diphtheria toxoid.

A number of scientific reports also show that good immunological reponses are obtained after administration of liposomes to the mucosa where the antigen is entrapped or adsorbed to liposomes.

Studies in vitro on a human cell line obtained from a colon cancer (Caco-2) shows that the best penetrating effect, tested with the model substance mannitol, can be seen with a chain length of 10 carbon atoms. In this case the lipids consisted of the salts of fatty acids. The obtained mixture of these lipids forms together with water micelles (Lindmark et al, J.Pharm.Exp.Ther. 275, 958–65, 1995).

Liposomes consists of phospholipids and are formulated by a relatively lengthy and cumbersome process which i.a. involves organic solvents. Furthermore, the phospholipids are expensive.

As described below in the present invention, a similar immunological response can be obtained only by mixing the antigen with a lipid formulation which contains less complicated lipids having a substantially lower price and which can be formulated on a commercial basis in a very simple way.

Another systems that to some extent are similar to the present invention are formulations based on triglycerides. However, these systems are scientifically defined as emulsions of triglycerides where surfactants are used for stabilization. As stabilizers phospholipids or any other type of amphiphilic molecules such as Tween® are normally used. Furthermore, the appearance of such emulsions are normally milky, indicating a size of the oil droplets of about 1 μm. It is well-known for the person skilled in the art that these surfactants are excellent adjuvants. Thus, the adjuvant properties of oil emulsions are primarily due to the characteristics of the surfactant and not of the triglyceride composition.

In PCT/DK94/00062 is disclosed a formulation for the topical administration of antigens and/or vaccines to mammals via the mucosal membranes. Said application disclose in the examples that the only formulation that enhances the immune response is a combination of caprylic/capric acid glycerides with polyoxyethylene sorbitan monoester (Tween 20®).

As exemplified in the present invention it is shown that a combination between a monoglyceride and a fatty acid can stimulate the immune system to produce antibodies and induce protective immunity. Furthermore the present invention shows that the disclosed formulation is able to produce high antibody titers by parenteral administration.

Thus, it was surprisingly found that the administration of antigens and/or vaccines to an animal either via the mucosal route or parenterally using a formulation comprising monoglycerides and/or fatty acids as a particulate lipid system can improve the immunological response towards the admixed antigens and/or vaccines. The monoglycerides are selected from a group with the general formula of 1-acyl-glyceride, wherein the number of carbon in the acyl chain may be varied between 8 and 24, preferably between 12 and 18. The acyl chain may be either saturated or unsaturated. The concentration of the monoglyceride may be in the range of 0.1–50 g per 100 ml of water, preferably in the range of 1–20 g per 100 ml of water. The fatty acid concentration may be in the range of 0.1–50 g per 100 ml formulation, preferably in the range of 1- 20 g per 100 ml water. When monoglycerides and fatty acids are formulated together the percent ratio of monoglyceride in fatty acid may be varied between 1 to 99%, preferably between 10 to 90%.

An enhancement of the immunological response after administration of monoglycerides and/or fatty acids together with antigens and/or vaccines has not been suggested anywhere in the prior art.

The present invention describes that mixtures of antigens with relevant lipids stimulates the body to generate protective immunity. Another advantage of the present invention is the simple formulation process and as compared to entrapment no material (antigen) is lost in the process. As an example can be mentioned that in the process of entrapment in liposomes the recovery is normally 10–20%. The rest is lost in the process.

Reports in the literature as discussed above, shows that by mixing liposomes and antigen an immune response is detected after administration to the mucosa.

However, the examples in this invention as described below shows that the system can be even more simplified by the use of lipids that are more stable, cheaper and which can be formulated to particles in a more convenient and simplified way.

The invention is exemplified by the following examples showing that the principle of co-administration of antigens, immune stimulating substances associated or in combination with particles function as an adjuvant.

EXAMPLE 1

A suspension of mono-olein was produced by adding 3 g mono-olein to 50 ml of a 0.6% Pluronic-127® solution in phosphate buffered saline pH 7.4, whereafter the mixture was sonicated with a probesonicator for 4 minutes. The obtained milky suspension contained particles with a maximal size of about 2 μm as determined by light microscopy.

EXAMPLE 2

A negatively charged micelle suspension of mono-oleate was produced by mixing of 0.5 g of oleic acid with 5 ml of 0.35 M NaOH and sonicated with a probesonicator for 5 seconds. Thereafter 3 g mono-olein and 50 ml 0.9% NaCl was added whereafter the mixture was probesonicated for 4 minutes. The monester content of the mono-oleate was over 95% with a acyl chain containing 92% oleate and 6% linoleic acid. The pH was adjusted to 8.3. The obtained completely clear homogenous solution contained particles with a size of below approximately 0.2 μm as determined by visual inspection. It is known that if a clear solution is obtained the particle size is below approximately 0.2 μm, a slightly opalescent bluish appearance indicated a size of approximately 0.2- 0.5 μm and if the appearance is milky the size is above approximately 0.8 μm.

EXAMPLE 3

A positively charged micelle suspension of mono-olein was produced by mixing 0.5 g lauryl-amine and 3.5 ml of 0.5 M HCl followed by sonication for 5 seconds. Thereafter 3 g mono-olein and 50 ml of water was added whereafter the mixture was probesonicated for 4 minutes. The pH was adjusted to between 4 and 5 using 0.5 M HCl. The obtained completely clear homogenous solution contained particles with a size of below approximately 0.2 μm.

EXAMPLE 4

A mixture of particles according to Example 1 and diphtheria toxoid was administrated subcutanously to mice followed by a booster after 21 days. After 30 days blood samples were obtained which were assayed for IgG antibodies against diphtheria toxin as well as Neutralization titers (NT) using Vero cells. The serum from Alum (n=5) and monoolein (n=5) groups was pooled and assayed. The mice receiving nasal boost and responded (=3 of 5) were assayed on an individual basis. In arbitrary units is shown in Table 1 the IgG titers and neutralization titers The results showed that both IgG as well as protective antibody titers were at the same level as compared to the control group which received the marketed product comprising diphtheria toxoid adsorbed on Alum (Al(PO$_4$)$_3$). Also seen is that high IgG titers always were accompanied by high neutralization titers indicating that the formulation does not destroy the antigenic sites that are important for protective immunity.

TABLE 1

|  | Dose diphtheria toxoid µg | IgG titer (arb. units) | NT titer (arb. units) |
|---|---|---|---|
| Alum | 15 + 15 | 32000 | 40000 |
| Alum | 3.5 + 3.5 | 22000 | 20000 |
| Mono-olein suspension | 15 + 15 | 24000 | 20000 |
| Mono-olein suspension | 3.5 + 3.5 | 3500 | 5000 |
| Nasal boost | 7 + 4 | 45000 | 10000 |
| Nasal boost | 7 + 4 | 19000 | 2500 |
| Nasal boost | 7 + 4 | 19500 | 5000 |

EXAMPLE 5

Particles were prepared according to Example 2 with a final concentration of monoglyceride of 200 mM and of fatty acid of 200 mM. Diphtheria toxoid (2.9 µl, 4.4 mg/ml) was mixed with 200 µl of the micelle suspension and administrated subcutanously to mice followed by a subcutaneous booster after 21 days. Both the primary and the booster dose of the toxoid was 10 µg. After 30 days blood samples were obtained which were assayed for IgG antibodies against diphtheria toxin. The result showed (Table 2) that the arbitrary IgG titers with respect to the formulation with mono-olein (MO) and oleic acid (C18:1) were at the same level as compared to the control group which received the present marketed product comprising diphtheria toxoid adsorbed on Alum (Al(PO$_4$)$_3$). The other combinations of monoglycerides and fatty acids gave slightly declining responses which correlated to declining length of the acyl chain (M12=lauryl-1-glycerate; M10=capric-1-glycerate; C12=lauric acid; C10=capric acid; C8=caprylic acid). N.D.=Not Done; indicates that there were only five mice in these groups.

TABLE 2

IgG response of individual mice (n = 5 or 6) after sc/sc administration of different formulations containing monoglycerides and fatty acids.

|  | 1 | 2 | 3 | 4 | 5 | 6 |
|---|---|---|---|---|---|---|
| Alum | 18200 | 18200 | 9600 | 9600 | 18200 | N.D. |
| MO/C18:1 | 18200 | 18200 | 18200 | 18200 | 9600 | N.D. |
| MO/C8 | 9600 | 9600 | 4800 | 9600 | 4800 | 9600 |
| M12/C12 | 18200 | 9600 | 4800 | 18200 | 9600 | 18200 |
| M10/C10 | 4800 | 110 | 2400 | 1200 | 2400 | 4800 |

EXAMPLE 6

The same procedure as in Example 4 with the difference that the booster dose was given nasally instead of subcutanously. The dose of diphtheria toxoid was 10 µg both at the primary immunization as well as at the nasal booster administration. In the same experiment a dose-response is demonstrated that is obtained when tree different amounts of lipid (see Table 3) was administrated. The arbitrary IgG titer is seen in Table 4. Besides the dose-response effect where lower IgG titers is seen at lower concentrations of lipids there is also seen a higher variability regarding response in the groups receiving lower doses. This variability is not seen at higher dose levels indicating that an adjuvant effect is not only seen with respect to obtaining high titers but also regarding reduction of the variability of the response.

TABLE 3

Amount of lipids in (µmol) administrated to mice sc or nasally.

| Dose level | Dose lipid (µmol) sc | Dose lipid (µmol) nasally |
|---|---|---|
| high | 40 | 1.5 |
| medium | 4 | 0.15 |
| low | 0.4 | 0.015 |

TABLE 4

IgG titers in individual mice (n = 6) after administration of 2 × 10 µg of diphtheria toxoid to mice either sc/sc or sc/nasally.

|  | 1 | 2 | 3 | 4 | 5 | 6 |
|---|---|---|---|---|---|---|
| MO/C8 sc/sc high | 4800 | 4800 | 9600 | 4800 | 9600 | 9600 |
| MO/C8 sc/nas high | 9600 | 1200 | 4800 | 4800 | 4800 | 9600 |
| MO/C8 sc/sc medium | 4800 | 1200 | 9600 | 2400 | 4800 | 4800 |
| MO/C8 sc/nas medium | 2400 | 600 | 2400 | 600 | 2400 | 4800 |
| MO/C8 sc/sc low | 300 | 2400 | 9600 | 2400 | 4800 | 2400 |
| MO/C8 sc/nas low | 600 | 600 | 1200 | 150 | 4800 | 150 |

EXAMPLE 7

Two different lipid formulation containing mainly medium length acyl chains (Composition A) and long acyl chains (Composition B) were tested. The compositions are seen in Table 5.

TABLE 5

|  | Monoglyceride | Fatty acid |
|---|---|---|
| Composition A | Monooleate 25 mM<br>Monomyristate 25 mM<br>Monolaurate 25 mM<br>Monocaprate 25 mM | Caprylic acid 90 mM |
| Composition B | Monooleate 200 mM | Oleic acid 200 mM |

The formulations were administrated to mice s.c. or nasally with a booster after three weeks s.c. or nasally. Blood samples were taken after another week. The arbitrary IgG titers are seen in Table 6.

The results in Table 6 demonstrates that in order to achieve a good response after primary as well as booster administration by the nasal route Compositions B is to be preferred.

TABLE 6

|  | 1 | 2 | 3 | 4 | 5 | 6 |
|---|---|---|---|---|---|---|
| Composition A sc/nas | 2400 | 4800 | 4800 | 18200 | 4800 | 4800 |
| Composition A nas/nas | <100 | 36400 | <100 | <100 | 300 | <100 |
| Composition B sc/nas | 18200 | 18200 | 36400 | 18200 | <100 | N.D. |
| Composition B nas/nas | 4800 | 9600 | 18200 | 18200 | 2400 | 9600 |

EXAMPLE 7

A mixture of mono-olein (200 mM) and caprylic acid (200 mM) was mixed with formalin inactivated influenza virus (strain SDA/94) and administrated s.c. at the first occasion to mice followed by a nasal booster three weeks later. The dose was 0.05 μg HA and blood sample were taken 3 weeks after the booster dose and assayed for agglutination titers (HI) against HA. The results (Table 7) showed that the HI titers in the group receiving the virus together with the adjuvants was at a higher level as compared to the group receiving the virus in PBS.

TABLE 7

HI titers in mice receiving formalin inactivated influenza virus after s.c. primary injection and nasal booster.

|       | 1    | 2   | 3   | 4   | 5    | 6  |
|-------|------|-----|-----|-----|------|----|
| PBS   | N.D. | 80  | N.D | 40  | N.D. | 80 |
| MO/C8 | 320  | 320 | 640 | 160 | 320  | *  |

N.D. = not detected
* = dead

EXAMPLE 8

Micelles according to Example 2 was mixed with formalin killed rota virus particles and subsequently administrated to female mice. After three immunizations the mice were made pregnant whereafter the new-born mice were challenged nasally with live rota virus. The figures indicate the animals that acquired protection after challenge as compared to the total number of animals in that group. The result from this challenge is seen in Table 8.

TABLE 8

Protection after challenge of rota virus to baby mice where the mother was vaccinated with a lipid formulation according to the invention.

| Group    | Administration | Protection |
|----------|----------------|------------|
| Saline   | im/im/im       | 2/8        |
| Micelles | im/im/im       | 4/4        |
| Micelles | im/nas/nas     | 6/7        |

As can be seen from the results there is a good protection both after three intramuscular administrations as well as after a primary intramuscular immunization followed by two nasal administrations.

EXAMPLE 9

To evaluate the toxicity of the lipid formulations these were administered into the rat nasal cavity whereafter the rats were killed and the nasal mucosa were prepared for light, fluorescence as well as scanning electron microscopy (SEM). Formulations according to Example 1 and Example 2 were tested. Only the mono-olein/pluronic suspension showed minor changes in the mucosal surface using the SEM. No effects could be detected under light or fluorescence microscopy. The micelles containing mono-olein and oleic acid were unable to provoke any changes in the mucosal membranes.

EXAMPLE 10

Caco-2 cells, which are a human cell line originating from a colon cancer can be made to grow as a epithelial mono layer. These cells are frequently used to examine different substances ability to influence the transport of biological substances through epithelial cells and has in a number of experimental systems been shown to give a good correlation to in vivo data regarding uptake from the gut into the bloodstream. As marker substances for transport through the cells Na-flouresceine or mannitol is used. The experiments with the lipid formulations according to this invention showed an enhanced transport through the Caco-2 cells at non-toxic concentrations.

The invention claimed is:

1. A method of immunizing a human or animal, the method comprising administering to a human or animal by mucosal administration a vaccine composition comprising an adjuvant consisting essentially of:
   i) monoolein
   ii) oleic acid and
   iii) water wherein the concentration of i) is from 0.1 g to 50 g per 100 ml of water, and the concentration of ii) is from 1 g to 50 g per 100 ml of water, and with the proviso that the percent weight ratio of i) in ii) is between 10 to 90, and an immunogenic quantity of an antigen component selected from the group consisting of diphtheria toxoid, influenza and rota virus antigen.

2. The method according to claim 1, containing in 100 g of the final vaccine composition:
   from 0.01 to 90 g antigen component selected from the group consisting of diphtheria toxoid, influenza or rota virus antigen,
   from 1 to 20 g of monoolein,
   from 1 to 20 g oleic acid,
   from 0.01 to 99 g water,
   from 0.01 to 99 g PBS or saline, and
   optionally one or more excipients.

3. The method according to claim 1, wherein the vaccine composition comprises additional pharmaceutical excipients selected from the group consisting of preservatives, osmotic pressure controlling agents, pH-controlling agents, organics solvents, enzyme inhibitors, water absorbing polymers, absorption promoters and anti- oxidative agents.

4. The method according to claim 1, wherein the purity of the monoolein is at least 90%.

5. The method according to claim 1, wherein the purity of monoolein is at least 95%.

6. A method according to claim 1, wherein the mucosal administration is to the mucosa of the nose, mouth, vagina, rectum or intestine.

7. A method according to claim 1, wherein the mucosal administration is to the mucosa of the nose.

* * * * *